United States Patent [19]

Holst et al.

[11] 4,144,886
[45] Mar. 20, 1979

[54] ABSORBENT LAMINATE

[75] Inventors: Arno Holst; Helmut Lask, both of Wiesbaden, Fed. Rep. of Germany

[73] Assignee: Hoechst Aktiengesellschaft, Fed. Rep. of Germany

[21] Appl. No.: 735,445

[22] Filed: Oct. 26, 1976

[30] Foreign Application Priority Data

Oct. 24, 1975 [DE] Fed. Rep. of Germany ....... 2547650

[51] Int. Cl.² .......................... A61F 13/16; B32B 3/26; B32B 5/18; B32B 21/06
[52] U.S. Cl. ..................................... 128/284; 428/87; 428/318; 428/321; 428/534; 428/536
[58] Field of Search ........................ 128/284, 285, 296; 428/87, 318, 321, 534, 536

[56] References Cited

U.S. PATENT DOCUMENTS

| 3,589,364 | 6/1971 | Dean et al. | 128/285 |
|---|---|---|---|
| 3,661,895 | 5/1972 | Germino et al. | 536/106 |
| 3,723,413 | 3/1973 | Chatterjee et al. | 260/17 R |
| 3,731,686 | 5/1973 | Chatterjee | 128/285 |
| 3,888,256 | 6/1975 | Studinger | 128/296 |
| 3,889,678 | 6/1975 | Chatterjee et al. | 128/285 |
| 3,965,091 | 6/1976 | Holst et al. | 260/17 A |
| 3,993,553 | 11/1976 | Assarsson et al. | 128/284 |
| 4,000,128 | 12/1976 | del Valle et al. | 536/106 |
| 4,044,766 | 8/1977 | Kaczmarzyk et al. | 128/285 |
| 4,066,828 | 1/1978 | Holst et al. | 128/296 |
| 4,068,067 | 1/1978 | Holst et al. | 128/296 |
| 4,069,177 | 1/1978 | Smith | 128/284 |
| 4,075,279 | 2/1978 | Holst et al. | 128/296 |
| 4,076,663 | 2/1978 | Masuda et al. | 128/284 |
| 4,090,013 | 5/1978 | Ganslaw et al. | 128/296 |

Primary Examiner—William R. Dixon, Jr.
Attorney, Agent, or Firm—James E. Bryan

[57] ABSTRACT

An absorbent laminate comprising a first layer of absorbent material and at least one layer comprising a tissue having an absorbent carbohydrate derivative on at least one face.

12 Claims, 4 Drawing Figures

ABSORBENT LAMINATE

This invention relates to an absorbent laminate, especially an article in sheet form, suitable for absorbing physiological body fluid, especially liquids.

Such laminar articles are used, for example, as sanitary towels, absorbent pads, undersheets for beds, diapers or diaper pants. They are required to absorb the quantities of fluid likely to occur in each case, and to retain as much of the absorbed material as possible.

To meet these requirements, soft materials, for example, muslin, were originally used, being subsequently boiled and repeatedly used. In recent years, however, for reasons both of convenience and of hygiene, the desire of consumers for absorbent laminar articles disposable after use simply by flushing away or by burning has prevailed to an increasing extent.

It has been proposed to meet the need by manufacturing laminated articles; disposable diapers, for example, are constructed from an interior cellulose flock layer, a surrounding tissue paper and finally a surrounding wet-strength covering fleece which is glued to itself on the underside. For a sheet or diaper pants the covering fleece is not so positioned that it surrounds the whole article, but is positioned only on one side and is bonded to a sheet or film that repels or is impermeable to body fluids and which forms the layer remote from the body.

The cellulose flocks are intended to absorb the physiological body fluids such as urine, blood and sweat, i.e. they must have good absorption properties. One great disadvantage of the articles made from the known absorbent laminar articles is that their retention, that is, their retention capacity towards liquids under pressure, is considerably less than their absorption capacity which for example in the case of diapers or diaper pants can lead to their having to be changed very frequently, involving more labor.

Since, as already stated, in particular the liquid retention of the laminar structures is inadequate, they are provided at least on the face nearer the body with a wet-strength covering fleece, which prevents a direct contact of the skin with the wet cellulose, but which is permeable towards liquids in both directions.

An absorbent pad for hygiene purposes with a layer of swellable material particles, for example polyacrylamide or sulfonated polystyrene, has been proposed in U.S. Pat. No. 3,888,256.

The present invention provides a laminated sheet material for absorbing physiological body fluids, comprising a first absorbent layer, preferably a cellulose flock layer and a tissue layer which has an absorbent carbohydrate derivative on at least one surface in the form of a coating; advantageously, the material also comprises a fleece, the tissue layer being positioned between the fleece and the first layer.

The coated tissues are made for example by bringing their surface to the desired moisture content by immersion of the paper for a short time in water and subsequently wiping the paper to remove excess liquid, and then coated with an absorbent carbohydrate derivative, for example by scattering a powder onto the damp surface, or in a vortex chamber, on one or both sides. Any carbohydrate in a comminuted, pourable form is suitable, regardless of whether the particles are fibrous, irregularly crumbly, or in any other manner comminuted. Preferably, modified cellulose ethers are used which have been modified according to the process of U.S. Pat. No. 3,936,441 by cross-linking, or which have been modified according to the process of U.S. Pat. No. 3,965,091, since they have a high water absorption and retention capacity. There may also be used, however, modified cellulose ethers, produced as described in U.S. Pat. Nos. 2,639,239, 3,723,413, and 3,589,364; cross-linked starch ethers are also suitable, for example, produced according to U.S. Pat. No. 3,661,895 and 4,000,128, starch grafted with acrylonitrile and subsequently saponified according to U.S. Pat. No. 3,661,815, and cellulose ethers produced from lacquered or unlacquered portions of cellulose hydrate foil produced according to U.S. Pat. No. 4,075,279 or cellulose ethers for example produced according to U.S. Pat. No. 3,678,031 which, owing to their low degree of substitution, lie just within the swelling range. This conversion of comminuted, swellable carbohydrate derivatives into a material which can be easily processed is described in detail in U.S. Pat. No. 4,096,312.

All these coated tissues have in common the fact that physiological body fluids or water cause them to swell considerably and permit fluid to pass towards a further absorbent system, for example, of one or more cellulose flock layers, but substantially prevent the fluid from flowing back in the reverse direction upon application of pressure, as exerted repeatedly, for example by a moving body, and in this manner increase the absorption and retention capacity of the total system. Such laminates have the advantage that in the case of laminar articles with large areas having only a relatively thin cellulose flock layer, the fluid is forced to distribute itself over the entire cellulose flock layer.

These advantages emerge clearly from the examples given below in which the articles are compared with untreated sheet-like laminar articles; improvements in the retention of urine of for example up to 45% and more are obtained. In addition according to the invention, the absorbent materials may be firmly fixed to the tissue and so cannot change their place of effectiveness within the article.

Various examples of articles constructed in accordance with the invention will now be described in greater detail with reference to the accompanying drawings, in which.

Figure 1:
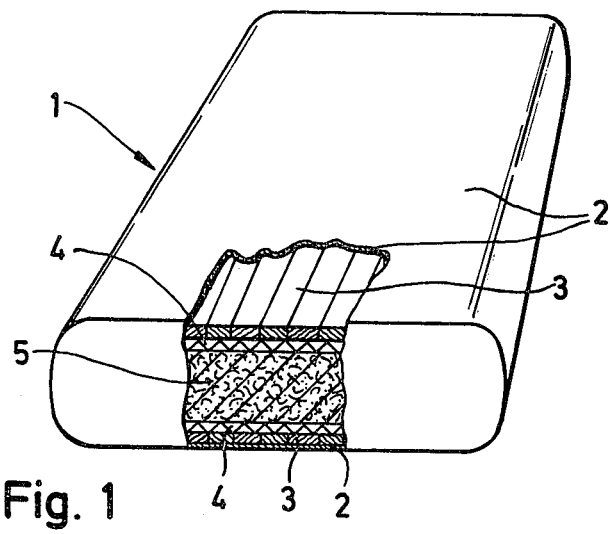
FIG. 1 illustrates a laminated article, the outer cover of which is partly removed to show the laminae.

Referring now more especially to FIG. 1, there is shown a laminar article indicated generally by the reference numeral 1, which is in the shape of a generally rectangular block having a covering fleece 2 extending all around its top, bottom, sides and ends. From top to bottom, as shown in the Figure, the inner layers comprise; a tissue paper layer 3, a coated tissue layer 4, and a cellulose flock layer 5. Then, working outwards again from the interior, there are further layers of coated tissue 4, tissue paper 3, and, as stated above, an exterior covering fleece 2.

The coated tissue layer or coated tissue layers 4 may in principle be arranged at all points inside the laminar article 1, but preferably they are located only on one side of one or more cellulose flock layers 5, or such that they enclose one or more cellulose flock layers 5.

Figure 2:
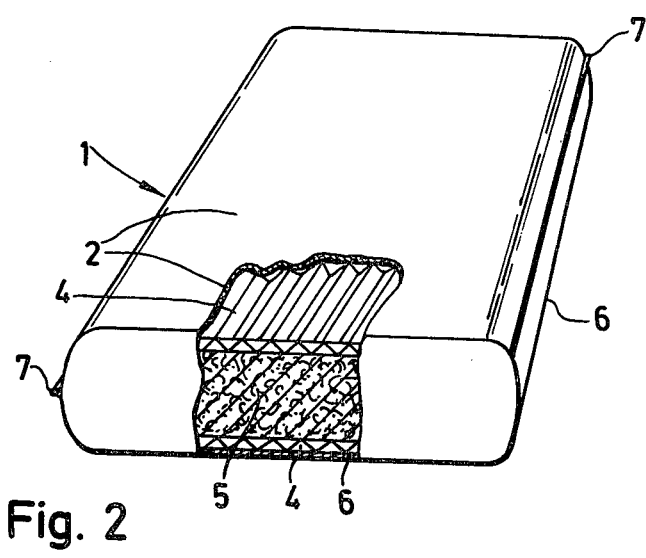
FIG. 2 illustrates a second form of article, different from FIG. 1 in having an additional liquid-proof layer.

A construction in which the article is designed not to allow moisture to pass through it to reach the area surrounding the body at all, if possible, is shown in FIG. 2. In this arrangement, there is added, on the side intended to be positioned remote from the body a film, 6, while the side nearest to the body has a covering fleece 2, fused along a line 7 to the film 6. The interior layers comprise, working inward, a coated tissue 4 encircling a cellulose flock pad 5.

Normally, the layers 4 are only needed on the side of the one or more cellulose flock layers 5 remote from the film 6.

If, in any embodiment, the one or more tissue layers 4 are coated only on one side with an absorbent carbohydrate derivative, then they are normally positioned in the article with their coated faces away from the surface of the article which will be lying nearest to the body.

Especially in the larger area articles, and depending on the efficiency of the coated tissue layers 4, it is not always necessary to position the layer 4 over the whole of the surface area; provision over the part of the area most heavily to be used is adequate.

Figure 3:
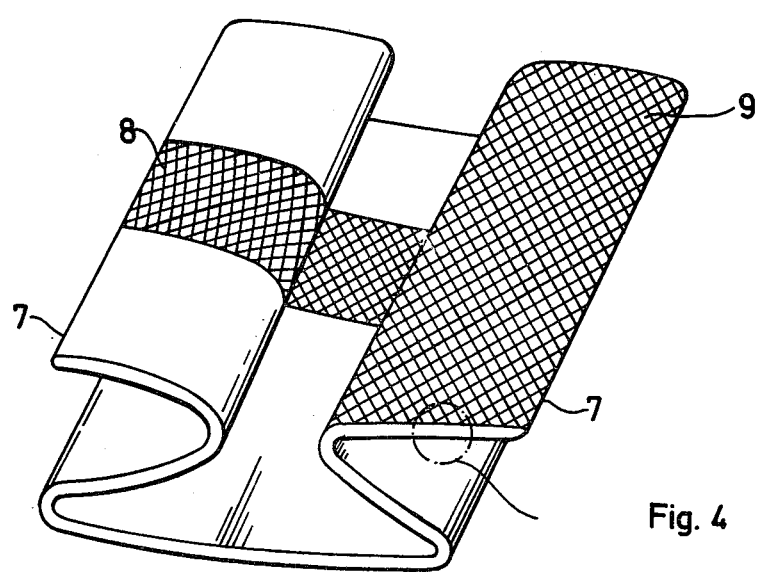
FIG. 3 illustrates two alternative types of pairs of diaper pants.

For example if, as seen in FIG. 3, the article 1 is to be used for the production of diaper pants, then the coated tissue layer 4 may occupy the surface area of the diaper pants within the laminar article either completely as shown by reference numeral 9, or only incompletely, that is, at the most heavily used point, as shown by reference numeral 8.

Figure 4:
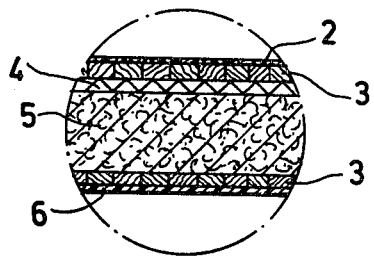
FIG. 4 is a section through part of the structure of FIG. 3 on an enlarged scale.

FIG. 4, a section through the portion 9 of FIG. 3, shows, reading down the Figure, a covering fleece 2, an uncoated tissue 3, a coated tissue 4, and a flock layer 5. On the other side of the flock layer 5, outward, there is an uncoated tissue 3 and a water-repellent film 6.

Laminar structures produced according to the invention can be used wherever physiological body fluids are to be absorbed and as far as possible retained, that is, in the hygiene field, in baby care, and in hospitals. They are especially preferred for the production of diapers, diaper pants and bed sheets. In use, they are arranged so that the coated tissue layers are generally located in the part of the article facing the body, between the covering fleece and the cellulose flock layer.

In the following Examples which illustrate the invention, percentage data refer to percent by weight, DS is the degree of substitution, relative to an anhydrous glucose unit, WRC is the water retention capacity in percent, measured against 2,000 times acceleration due to gravity, relative to the water-insoluble portion of the entire product; it is determined after immersion of the sample in water.

EXAMPLE 1

A 100 cm$^2$ piece, 8.3 cm wide, 12 cm long and weighing about 7.1 g is cut from a commercially available diaper and a tissue coated on one side is inserted in it so that it is located only on one side between the covering fleece and the cellulose flock layer, its coated side facing the cellulose flock layer. 60 grams of synthetic urine solution are uniformly dropped from a burette onto the surface of this "test article" lying nearest to the coated tissue. After waiting 15 minutes for this application to take effect, the piece of diaper is covered with a piece of diaper of the same size to absorb the fluid and the complete article is subjected to a pressure of 50 pounds/cm$^2$ for 15 minutes. Subsequently, the diaper piece which has been placed on this first piece is removed and the amount of fluid remaining in the "test article" is determined analytically by weight; about 75% of synthetic urine solution remain behind.

The above-used coated tissue is produced as follows: a tissue web 120 mm wide and having a weight per unit area of 25.7 g/m$^2$ is drawn through water and after wiping away the water adhering to it is passed through a vibrating laboratory sifter. The carboxymethyl cellulose to be applied to one side has been cross-linked with bisacrylamido acetic acid and has a WRC of 6, 300% at a DS of 0.75; it is sprinkled on through a 0.2 mm mesh sifter such that 0.6 g of the cross-linked carboxymethyl cellulose is attached to a 100 cm$^2$ piece of tissue.

COMPARATIVE EXAMPLE

A "test article" is made and treated as described in this example but instead of the coated tissue an uncoated tissue is inserted. About 52% of the amount of synthetic urine remain behind when tested as described. The substitution of the coated tissue therefore improves the urine retention by about 45%.

EXAMPLE 2

After first removing its film, there is cut from a typical commercially available pair of diaper pants a piece 100 cm$^2$, 8.3 cm wide by 12 cm long, and having a cellulose flock composition of 3.6 g and having a covering fleece. A "test article" is now produced by placing the piece on a piece of film capable of repelling body fluid and having a width of 10.3 cm and a length of 14 cm with the fleece in contact with the film. A tissue coated on one face is inserted between the covering fleece and the cellulose layer, with its coated face facing the cellulose flock layer. The film is then fused to the fleece so that a close system is formed which is denoted as a "test article". Onto the surface of the "test article" remote from the film there is dropped from a pipette 6 ml of synthetic urine solution; after 3 minutes waiting time and 3 minutes subjecting it to 20 p/cm$^2$, another 6 ml of urine solution are applied and there is another 3 minutes waiting time and 3 minutes stressing time. After a further 5 minutes 20 sheets of filter paper are placed on it and the whole article is subjected to 20 p/cm$^2$ for 15 minutes. After removing the filter papers the fluid remaining in the "test article" is determined analytically by weight; 97% of the 12 ml of synthetic urine solution remain in the diaper.

The coated tissue used above is produced as follows: A tissue web 120 mm wide and having a weight per unit area of 25.7 g per square meter is passed through water and after wiping away the water adhering to it is passed through a vibrating laboratory sifter. The carboxymethyl cellulose to be applied to one side has been cross-linked with bisacrylamido acetic acid and has a WRC of 11,800% at a DS of 1.08; it is dusted on through a 0.2 mm mesh sifter to provide 5.9% of cross-linked carboxymethyl cellulose on a 100 cm$^2$ piece of tissue in the "test article", relative to the cellulose flock composition thereof.

COMPARATIVE EXAMPLE

A "test article" is produced and treated as described above in this example, but using an uncoated tissue instead of the coated tissue. Of the 12 ml of the synthetic urine solution applied there remain 46% in the diaper.

EXAMPLE 3

A "test article" is produced and treated as described in Example 2, except that the tissue has a coating of 5.6% cross-linked carboxymethyl cellulose based on the weight of the cellulose flock and 12 ml of synthetic urine solution are applied thereto twice. Of the 24 ml of synthetic urine solution applied 89% remain in the diaper. In a comparison, using an uncoated tissue, of the 24 ml of the synthetic urine solution applied, 32% remains in the diaper.

EXAMPLE 4

A "test article" is produced and treated as described in Example 2 but is provided with a cellulose flock composition of 5.1 g and a coating of the tissue such that afterwards in the "test article", relative to the cellulose flock composition thereof, there is about 8.1% of cross-linked carboxymethyl cellulose. Of the 12 ml of synthetic urine solution applied there remain 96% in the diaper.

EXAMPLE 5

A "test article" is produced and treated as described in Example 2, but is provided with a cellulose flock composition of 5.0 g, an insert of the tissue coated on one side on the side between the film and the cellulose flock layer, and such a coating of the tissue, that afterwards there is about 8.6% of cross-linked carboxymethyl cellulose in the "test article", relative to the cellulose flock composition thereof. Of the 12 ml of synthetic urine solution applied, 55% remain in the diaper.

EXAMPLE 6

In examples corresponding otherwise to those of Examples 2 and 3, the lowest of the filter paper sheets inserted to absorb the urine is rendered hydrophobic with a commercially available baby cream, intended to simulate the clean skin of a baby. If the urine absorptions of the filter papers in the case of "test articles" without coated tissue are taken as zero values, then an average absorption of synthetic urine by the filter papers of 0.8 g per 100 cm$^2$ of article surface is obtained. If the procedure is repeated with the coated tissue between the cellulose flock layer and the film, then a considerably higher average absorption of synthetic urine by the filter papers of 2.4 g per 100 cm$^2$ of article surface is obtained. The urine retention is naturally accordingly lower.

It will be obvious to those skilled in the art that many modifications may be made within the scope of the present invention without departing from the spirit thereof, and the invention includes all such modifications.

What is claimed is:

1. In an absorbent laminate comprising a first layer of cellulose flock, at least one layer of a tissue having an absorbent carbohydrate derivative on at least one face and a covering fleece, the tissue layer being positioned between the fleece and the first layer, the improvement comprising that the absorbent carbohydrate derivative is selected from the group consisting of a crosslinked cellulose ether, a crosslinked starch ether, and a starch grafted with acrylonitrile and subsequently saponified.

2. A laminate as claimed in claim 1, wherein the carbohydrate derivative is a crosslinked cellulose ether.

3. A laminate as claimed in claim 1, wherein the carbohydrate derivative is cross-linked carboxymethyl cellulose.

4. A laminate as claimed in claim 1, wherein the tissue layer is coated with carbohydrate derivative on one face only and the coated face is towards the first layer.

5. A laminate as claimed in claim 1, wherein the tissue covers a part only of any surface of the first layer.

6. A laminate as claimed in claim 1, having tissue on both sides of the first layer.

7. A laminate as claimed in claim 1, wherein the tissue is on one side only of the first layer.

8. A laminate as claimed in claim 1, which also comprises an uncoated tissue layer between said covering fleece and said tissue layer having an absorbent carbohydrate derivative thereon.

9. A laminate as claimed in claim 1, which comprises a film, substantially impervious to moisture, positioned as one outer face of the laminate.

10. A laminate as claimed in claim 1, in the form of a diaper, diaper pants, or a bed sheet.

11. An absorbent laminate comprising a first layer of cellulose flock having on at least one face a tissue layer coated with an absorbent carbohydrate derivative selected from the group consisting of a crosslinked cellulose ether, a cross-linked starch ether and a starch grafted with acrylonitrile and subsequently saponified, an uncoated tissue, and a covering fleece, in the order stated.

12. An absorbent laminate comprising a first layer of cellulose flock having on one face, in succession, a tissue layer coated with an absorbent carbohydrate derivative selected from the group consisting of a crosslinked cellulose ether, a cross-linked starch ether and a starch grafted with acrylonitrile and subsequently saponified, an uncoated tissue and a covering fleece, and having on the other face an uncoated tissue and an impervious film.

* * * * *